United States Patent [19]

Saurer

[11] Patent Number: 5,407,554
[45] Date of Patent: Apr. 18, 1995

[54] ELECTROCHEMICAL SENSOR WITH MULTIPLE ZONES ON A DISC AND ITS APPLICATION TO THE QUANTITATIVE ANALYSIS OF GLUCOSE

[75] Inventor: Eric Saurer, Bevaix, Switzerland
[73] Assignee: Asulab S.A., Bienne, Switzerland
[21] Appl. No.: 224,778
[22] Filed: Apr. 8, 1994

[30] Foreign Application Priority Data

May 10, 1993 [FR] France ................. 93 05683

[51] Int. Cl.⁶ ............................. G01N 27/26
[52] U.S. Cl. ................... 204/403; 204/412; 204/416; 204/418; 204/419; 435/291; 435/817; 422/68.1; 422/82.03
[58] Field of Search ............... 204/403, 412, 416, 418, 204/419; 435/291, 817; 422/68.1, 82.03

[56] References Cited

U.S. PATENT DOCUMENTS

| 4,963,245 | 10/1990 | Weetall | 204/153.1 |
| 5,066,372 | 11/1991 | Weetall | 204/153.1 |
| 5,228,972 | 7/1993 | Osaka et al. | 204/415 |

FOREIGN PATENT DOCUMENTS

| 0170375 | 2/1986 | European Pat. Off. . |
| 0406304 | 9/1989 | European Pat. Off. . |
| 2127142 | 12/1971 | Germany . |
| WO89/08713 | 9/1989 | WIPO . |
| WO92/14741 | 9/1992 | WIPO . |
| WO92/14836 | 9/1992 | WIPO . |

OTHER PUBLICATIONS

Marine Technology, Liu et al., 'Miniature multiple cathode dissolved oxygen sensor ...', vol. 16, 1980, pp. 468–472.

Primary Examiner—John Niebling
Assistant Examiner—Bruce F. Bell
Attorney, Agent, or Firm—Pollock, Vande Sande & Priddy

[57] ABSTRACT

An electrochemical sensor having multiple measuring zones (34) that are sequentially insulatable, disposed on the circumference of an insulating disc (1) and associated with each other by peripheral current collectors (16, 17) which extend radially inward up to central zones where they form contacts (23, 24) for a measuring apparatus. The disc-sensor also has a device (6) for rotating the disc, and guide marks for positioning (11) and for isolating (7) the measuring zones (34), and may be contained in a housing (40). The invention is useful in the quantitative analysis of glucose.

20 Claims, 6 Drawing Sheets

ELECTROCHEMICAL SENSOR WITH MULTIPLE ZONES ON A DISC AND ITS APPLICATION TO THE QUANTITATIVE ANALYSIS OF GLUCOSE

FIELD OF THE INVENTION

It is the object of the instant invention to provide an electrochemical sensor having, on the same thin, insulating, rigid support that is disc-shaped and small, several active zones traversed by the same set of electrodes making it possible to execute several successive measurements of the same parameter using a single sensor introduced into an appropriate measuring apparatus.

The object of the instant invention is more specifically an amperometric sensor adapted to measure the level of glucose in the blood.

DESCRIPTION OF THE PRIOR ART

Numerous electrochemical techniques have been developed to detect the physico-chemical characteristics of a medium using electrodes and a suitable electrical or electronic circuit, or to determine the concentrations of substances present in solutions, effluents or fluids of natural, biochemical or biological origin. A feature common to these techniques is the use of at least two electrodes to effect measurements using conductimetry, voltametry, amperometry or polarography with the intervention, if necessary, of a reagent added to the medium or confined in the vicinity of an electrode.

For the quantitative analysis of glucose in the blood, the above-mentioned reagent will comprise at least one enzyme specific to glucose, preferably associated with a mediator.

The generation of bulky laboratory apparatus that are expensive and may only be used by qualified personnel has been succeeded by smaller, and even portable, apparatus provided with electrode devices designated under the general term "sensor".

The first small electrochemical sensors, separable from the measuring apparatus and hence disposable, appear to have been described by Miles Laboratories Inc. in German patent application DE 2 127 142 claiming a priority of June 1970. The device described in this application relates to an electrochemical sensor in which two electrodes are arranged horizontally on a small-sized insulating plate using a thin-layer deposition technique.

It is also possible to cite numerous publications by C. C. LIU, M. R. NEUMAN et al (Marine Technology 16 (1980) 468–472; Diabetes Care Vol. 5, No. 3, May–June 1982) relating to research aimed at perfecting miniature sensors and at notably permitting the quantitative analysis of blood glucose using sensors that may be disposed of after each use.

Numerous other documents describe specific embodiments of sensors of this type, not always having a single measuring zone, connectable to a measuring apparatus and disposable after first use. European patent EP 0 406 304, for example, describes a sensor provided with superimposed electrodes.

When there are several measuring zones, there is always a juxtaposition of several discrete sensors, each sensor being provided with its own system of connection to a measuring apparatus. An example of this type of embodiment is given in European patent EP 0 170 375.

French patent application FR 93 01331 in the name of the applicant, incorporated by reference in the instant application, constitutes an additional step in the development and in the principle of the above-mentioned sensors in that the sensor described is composed of a succession of active zones disposed on an insulating substrate in the form of a band, said active zones all being associated with each other up to a common connection zone with the measuring apparatus, each zone being sequentially detachable from the support band after the measurement has been effected. Compared to previously known sensors, a device of this type offers numerous advantages for the user who may effect several measurements before placing a new sensor in the apparatus. It is nonetheless obvious that the number of measurements which the user may carry out with a single sensor, when this latter has a substrate of rigid material, is limited by the dimensions of the measuring apparatus adapted to receive said sensor. If it is desired to carry the measuring apparatus in a pocket of a garment, the largest dimension of the measuring apparatus, and hence of the band-shaped sensor, will be of the order of 15 cm and said sensor will then have at most five to six active zones aligned on the same band.

OBJECTS OF THE INVENTION

In contrast, one of the objects of the invention is to provide a sensor also having several active zones, said zones no longer being aligned, but disposed on an external border of a small rigid disc of insulating material while still having a common connection close to the centre of the disc, said connection permitting connection to a measuring apparatus for the duration of use of all the active zones. A sensor of this type according to the invention will hereinafter be designated by the general term "disc-sensor".

Another object of the invention is to obtain a sensor having, for a given diameter, a larger number of active zones than a multizone band sensor, the length of which is identical to the diameter of the sensor of the invention.

Another object of the invention is to provide a sensor, the active zones of which can be sequentially isolated after each measurement of the other active, still unused zones without its being necessary to completely detach them from the supporting disc.

Another object of the invention is to provide a sensor device in which the disc-sensor is protected by a housing enveloping the disc while still permitting its manipulation, its positioning in the measuring apparatus as well as its electrical connection to the electronic circuit of the measuring apparatus, its driving in rotation to position and present the successive measuring zones and the isolation of the measuring zones used from other, still unused, measuring zones.

BRIEF SUMMARY OF THE INVENTION

The disc-sensor with sequentially isolatable multiple active zones according to the invention is composed of a rigid disc of an insulating material of small thickness on which are disposed at least two current collectors of conducting material, electrically insulated, on the same face or on the opposing faces to constitute a connection zone close to the center of the disc and to connect the active zones situated at its periphery by constituting in these zones the electrodes which make it possible to effect the electrochemical measurements.

BRIEF DESCRIPTION OF THE INVENTION

The material used to form the insulating rigid disc will for example be a synthetic resin such as a vinyl resin, ceramic, mica, a polyethylene terephthalate or glass; depending on the insulating material used, the disc is given its desired shape by molding, stamping, cutting or any other suitable process. To be able to be used in a measuring apparatus that may easily be carried in the pocket of a garment, the disc has a thickness comprising between 0.5 and 6 mm and a diameter comprising between 5 and 15 cm, preferably between 6 and 12 cm. It is clear that the diameter of the disc will also be a function of the number of active zones desired on the same disc, given that a minimum distance of about 10 to 20 mm is needed to prevent a measuring zone just used from disturbing still unused measuring zone(s). It is thus possible to produce disc-sensors having between 6 and 24 active zones, and preferably between 8 and 12 active zones. For a disc about 7 cm in diameter, it will for example be possible to arrange 8 measuring zones on the same face of the disc.

Current collectors are arranged on one face or on both faces of the disc according to a defined configuration by known deposition techniques, termed thin or thick layer, of suitable conducting material; these collectors may also be disposed on the disc by lamination of an insulating film coated with said conducting material. The appropriate conducting material used may, for example, be gold, silver, platinum, nickel, palladium, titanium or carbon.

When the disc-sensor of the invention is intended for the quantitative analysis of glucose in the blood, a current collector has portions constituting the reference electrode. The conducting material used for the working electrode is one of the above-mentioned metals, as well as carbon; the conducting material of the reference electrode is generally silver coated by a layer of silver chloride. According to methods well known in the prior art, such as those described in application WO 92/14 836, the working electrode also has a reagent comprising am least one oxidoreduction enzyme specific to glucose (GOD) and at east one mediator permitting the transfer of electrons between said enzyme and said current collector. The suitable mediator used is, for example, a complex of a transition metal with at least one bipyridine, terpyridine or phenanthroline ligand substituted by at least one electron donor group, such as those described in patent WO 92/14 741.

When the current collectors are supported by the same face of the disc they are then disposed in the form of two concentric rings, electrically insulated from one another, located inside a narrow border at the periphery of the disc, one ring at least located closest to the centre being open, the two rings being connected by radial extensions from the current collectors at the central zone where the connection is effected to a measuring apparatus. The active zones are distributed in the peripheral border, in equal sectors, and are delimited across the current collectors, either by deformation of the insulating support disc, or by windows provided in an insulating covering film. The portions of current collectors situated inside the zones thus delimited constitute the electrodes of each active zone.

When the insulating support disk and the current collectors are covered by an insulating covering film, this latter also has windows rendering the contact zones situated close to the centre and the windows between each active zone accessible, leaving visible portions of the two collectors which will be stamped or cut, by a device integrated in the measuring apparatus so as to isolate a used active zone from the other, still unused active zones.

The connection zones situated close to the centre of the disc and extending the extremities of the extensions of the current collectors are either composed of small surfaces in the shape of pastilles, or by a border or a concentric disc.

The disc-sensor is also provided with drive means in its center, at its periphery or on one of its faces.

When the drive member is situated in the center, this advantageously permits the associated drive member of the measuring apparatus also to ensure the connection with the contact zones of the current connectors, regardless of whether these zones are shaped like a crown, or of pastille shape at the extremities of the extensions of the current collectors. This central drive member will be advantageously composed of a hole passing through the disc having a regular polygon section, or an irregular polygon if the embodiment of the disc-sensor requires recovery of the first active zone to be used.

When the drive member is situated at the periphery, it is for example composed of indentations around the edge of the disc-sensor, adapted to cooperate with a toothed wheel of the measuring apparatus.

When the drive member is located on one face of the disc, it may be located on the face having active zones if the disc-sensor has an insulating cover covering the current conductors, but it will be more advantageously located on the opposing face. This drive member will for example be composed of a notched crown or by a friction wheel formed at the same time as the disc or mounted thereon.

If the drive member does not make it possible to ensure centering of the disc-sensor in the measuring apparatus at the same time, supplementary means are provided, such as a ring or an axle. The centering may also be effected, if the embodiment of the disc-sensor permits, by means of a seating adapted to receive said disc.

To avoid the same zone being used twice in succession, the drive mechanism of the measuring apparatus may be designed for this purpose.

The disc-sensor itself may also very simply be provided, at its periphery or on one of its faces, with an anti-return catch and with a portion of radial rib preventing the disc from making more than one revolution. The portion of radial rib may also constitute the drive member of the disc-sensor, by cooperating with a groove of a rotating piece of the measuring apparatus.

Similarly, the drive device of the measuring apparatus may be adapted so that each manipulation only drives the disc-sensor by one step corresponding to the passage from one active zone to another. The disc-sensor may also itself have positioning members composed of recesses provided in the edge of the disc, between each active zone and with the same step as that existing between one active zone and the next.

The number of active zones carried by one face of the disc will naturally be a function of the diameter of the disc itself. As may be seen in the following examples, for a small disc-sensor, that is for a measuring apparatus that can be carried in a pocket of a garment, this number could vary between 5 and 18, or more if the embodiment makes it possible to use the two faces of the disc.

When the current collectors are disposed on opposing faces of the disc they are distributed in a star-shaped pattern as from a disc or from a central crown constituting the contact zone. The measuring zones are then entirely on the periphery. The embodiments mentioned hereinabove for a disc-sensor having both current collectors on the same face are also applicable to a disc-sensor having the collectors on each face, nonetheless excluding a device driven by indentations at the edge. When the current conductors are disposed in a star-shaped pattern on each face of the disc, the active zones may also be isolated after each measurement by breaking them along a preshaped contour. In an embodiment of this kind, the disc-sensor will for example have at its periphery radial notches extending up to a circular zone weakened by a groove.

To protect the active zones and to facilitate manipulation of the disc-sensor and its positioning in the measuring apparatus, the disc-sensor may be contained in a housing the shape of which is round or square or which has a shape combining these two shapes. The housing is provided with an opening providing access to a single active zone, with an opening permitting the crimping of the current collectors, with one or two openings providing access to the contact zones and, if necessary, with a supplementary opening providing access to the drive device. The housing also has on its inside faces members that cooperate with corresponding members of the disc-sensor to contribute to the centering thereof. The housing also has, on one inside face, or on both depending on the embodiment, a continuous or discontinuous crown adapted to bear against a single face of the disc-sensor, or against both of them depending on the embodiment, so as to guide the disc-sensor in rotation, whilst maintaining it slightly separate from the lower and higher inside walls of the housing. When the housing is perfectly round, a rib may be provided on one of its external faces to facilitate positioning in the measuring apparatus.

BRIEF DESCRIPTION OF THE DRAWINGS

The invention will be better understood with reference to the embodiments such as those shown in the appended figures, in which.

In all the sectional representations, the proportions between the thickness of the different layers and their surface have been disregarded to facilitate comprehension of the arrangement of the different layers; similarly, the rear parts of the insulating coverings removed have not been shown.

In all the figures, similar parts of the disc-sensor or of the housing bear the same reference, regardless of the embodiment.

In the figures containing repetitive elements, only one or two elements bear a reference.

DETAILED DESCRIPTION OF THE INVENTION

Figure 1:
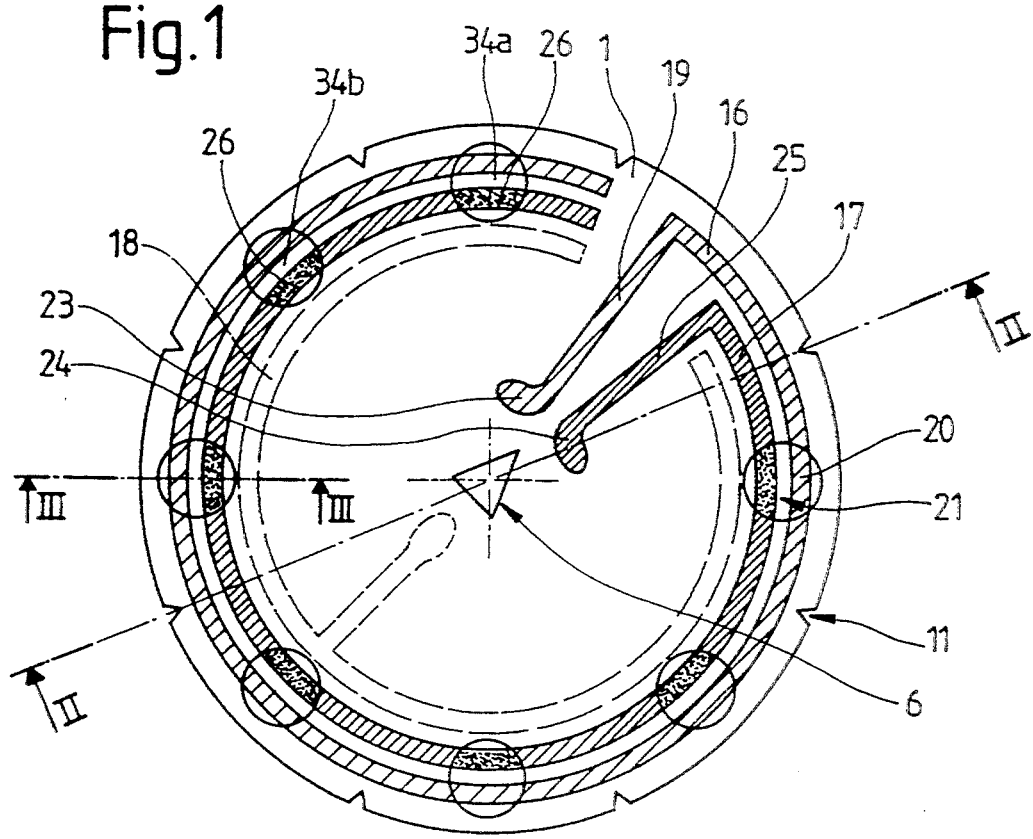
FIG. 1 shows a plan view of a first embodiment of a disc-sensor according to the invention.
Figure 2:
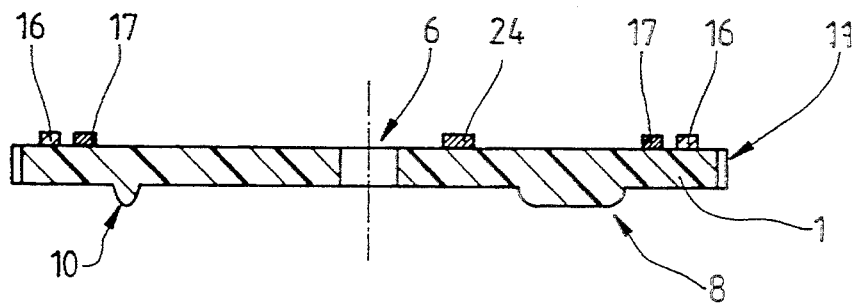
FIG. 2 shows a section diametral to FIG. 1 along the line II—II.
Figure 3:
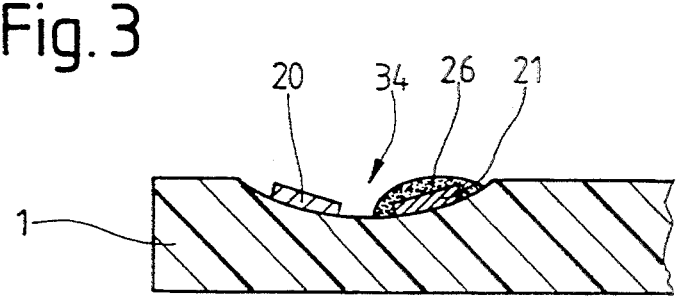
FIG. 3 shows a partially enlarged diametral section through the center of an active zone along the line III—III.

According to a first embodiment, shown in FIGS. 1 to 3, the sensor is composed of a support disc 1 of insulating material having a thickness of the order of 1 mm and a diameter of 7 cm. This disc is preshaped by stamping to have at its periphery positioning recesses 11 regularly spaced at angles of 45° thus defining eight equal circular sectors. The zones constituting the measuring zones 34 are delimited inside seven of these sectors, in their median axis and close to the periphery. In its center, the disc 1 is pierced by a drive mechanism 6 in the form of a hole shaped like an isosceles triangle having its axis of symmetry aligned with that of the eighth circular sector. On the surface of this disc and close to its periphery there are disposed two current collectors 16, 17 shown for purposes of simplification in the form of two open concentric narrow rings, each of which has at one of its extremities a radial extension 19 or 25 directed towards the center, in a the circular sector not having a measuring zone 34, where it terminates as a small pastille-shaped surface constituting a contact zone 23 or 24. Starting from the proximity of the center, where they will be connected to the measuring apparatus by the contact zones 23, 24, the current collectors 16, 17 thus pass successively through the seven measuring zones 34 inside which they constitute the electrodes 20, 21.

When the disc-sensor is intended to carry out blood glucose level measurements, each measuring zone 34 also has a reagent 26 deposited on the working electrode 21, by known pipetting, serigraphic or transfer techniques, as shown in the enlarged view of FIG. 3. It may also easily be imagined that the measuring zones 34 may have between the electrodes 20 and 21 a small excess thickness created when the disc is formed to facilitate deposition of the reagent 26. Reference now being made to FIG. 1, it will also be noted that the disc 1 may have more than two electrodes, for example a third reference electrode 18 shown with dotted lines formed, in common with the two electrodes 16 and 17, of an open ring, having at any point of said ring a radial extension directed towards the center and having at its extremity a small pastille-shaped surface forming a contact zone.

FIG. 2 is a section showing two characteristic elements of the face of the disc 1 not supporting the current collectors. The reference 10 shows in section one of the bosses located on the circumference of a circle so as to facilitate free rotation of the disc in the measuring apparatus; this succession of bosses may also be replaced by a continuous circular rib intended on the one hand to position the first measuring zone to be used 34a, on the other hand to limit the rotation of the disc 1 to one revolution, cooperating with a corresponding rib located in the measuring apparatus so as to prevent a measuring zone becoming presented again for a new measurement. The drive of the disc may be effected by a member of the measuring apparatus cooperating either with the drive mechanism 6, or with the rib 8.

The separation of a used measuring zone—for example 34a—from an unused measuring zone—for example 34b—is effected by a means on the measuring apparatus itself which crimps the two current collectors 16, 17 or cuts the disc along one of its spokes between the two zones 34a and 34b at a point located by means of the recesses 11.

Figure 4:
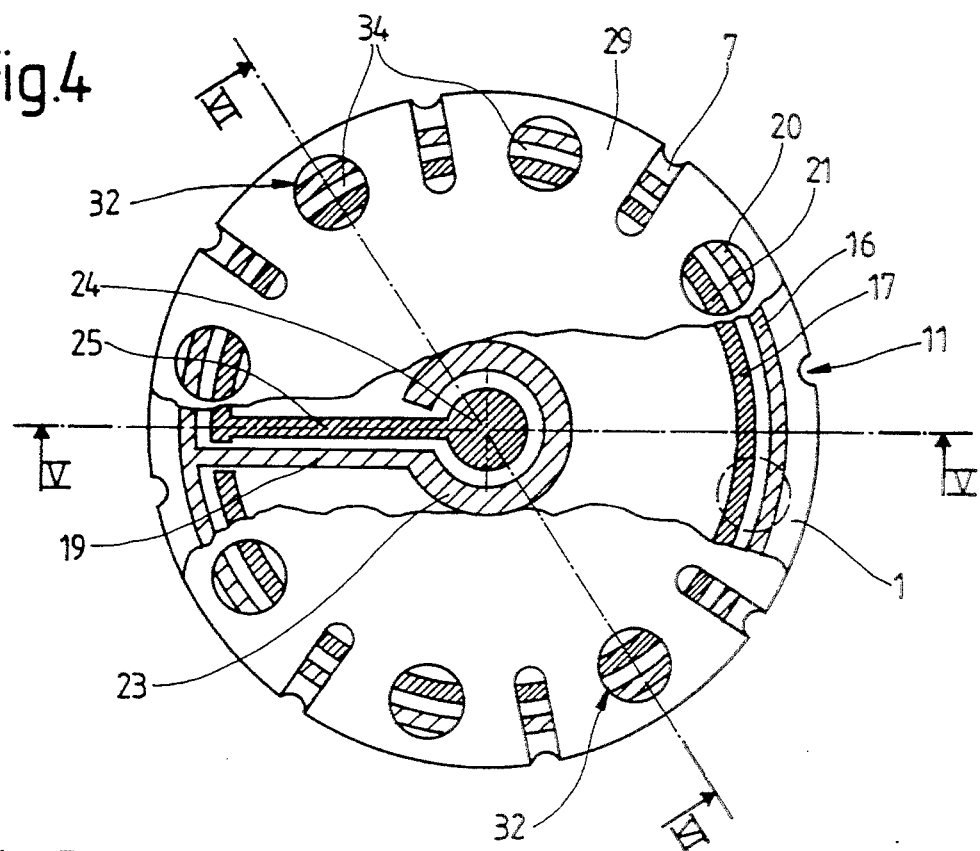
FIG. 4 shows a plan view of a second embodiment in which the upper covering has been partially removed.
Figure 5:
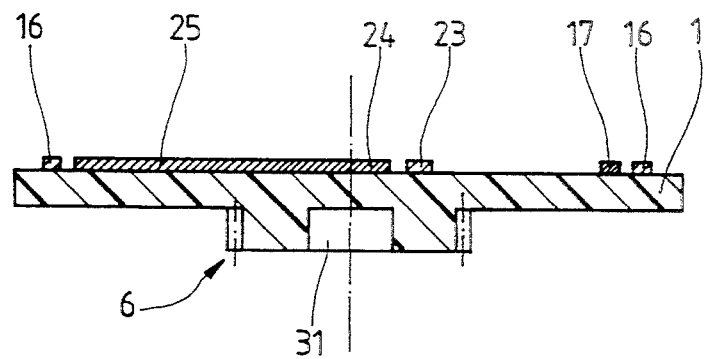
FIG. 5 shows a diametral section of FIG. 4 along the line V—V.
Figure 6:
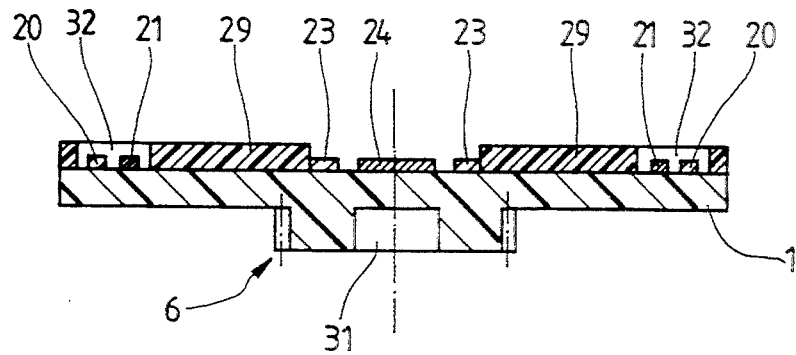
FIG. 6 shows another diametral section of FIG. 4 along the line VI—VI.

The disc-sensor corresponding to a second embodiment shown in FIGS. 4, 5 and 6, similarly has a disc 1 divided into eight equal circular sectors, each of the eight sectors being occupied by a measuring zone 34, each measuring zone being delimited by a window of the same dimension provided in an insulating covering film 29. Apart from the windows corresponding to the measuring zones, said covering film also has a window 32 at the level of the contact zones 23, 24 and windows 7 forming isolating zones regularly spaced close to the periphery of the disc, and revealing small portions of the collectors 16, 17 which could be crimped in these zones to insulate a used measuring zone. Due to the insulating covering film 29, the radial extensions 19, 25 may be brought closer to a measuring zone and be situated in a smaller circular sector comprised between a measuring zone 34 and a window 7, thereby permitting occupation of all the circular sectors by eight measuring zones. According to the embodiment of this variant, the contact zones 23, 24 are composed of a disk located in the center and of an open concentric ring. The drive mechanism 6 will then be composed, for example, of a pinion located on the face of the disc not supporting the collectors and attached by bonding or resulting from forming of the disc.

Figure 7:
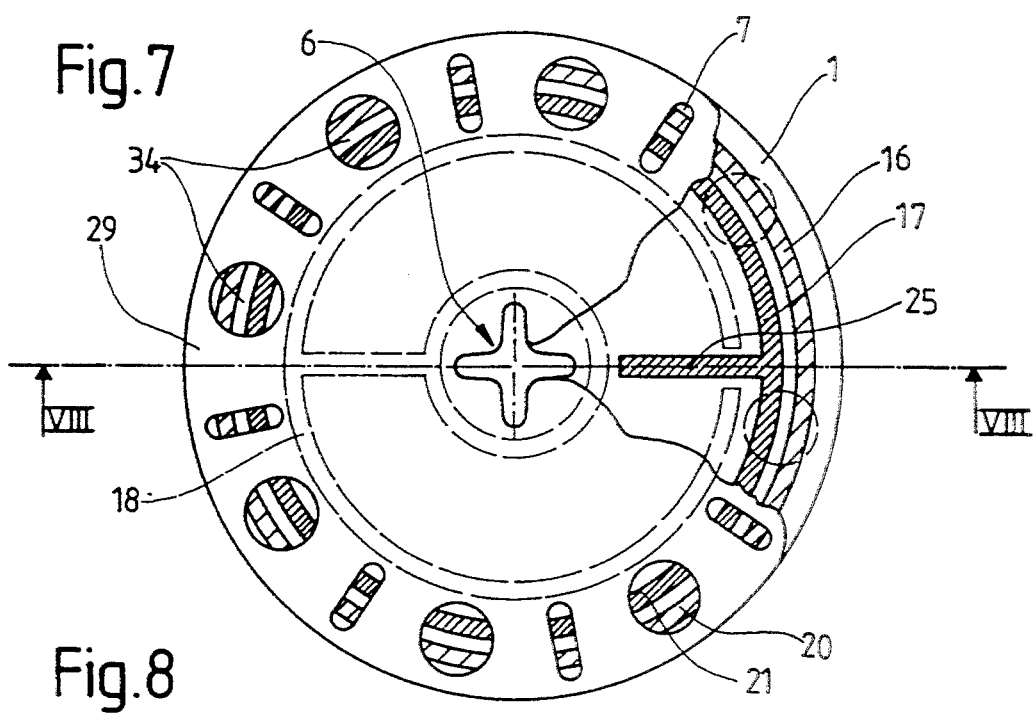
FIG. 7 shows a plan view of a third embodiment in which the upper covering of the disc-sensor has been partially removed.
Figure 8:
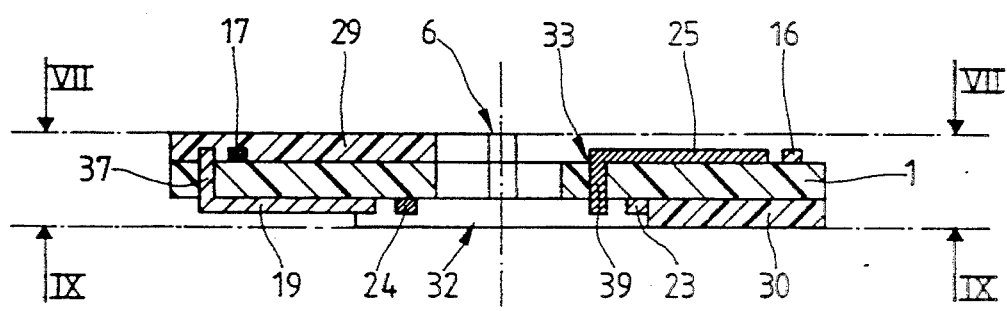
FIG. 8 shows a diametral section of FIG. 7 along the line VIII—VIII.
Figure 9:
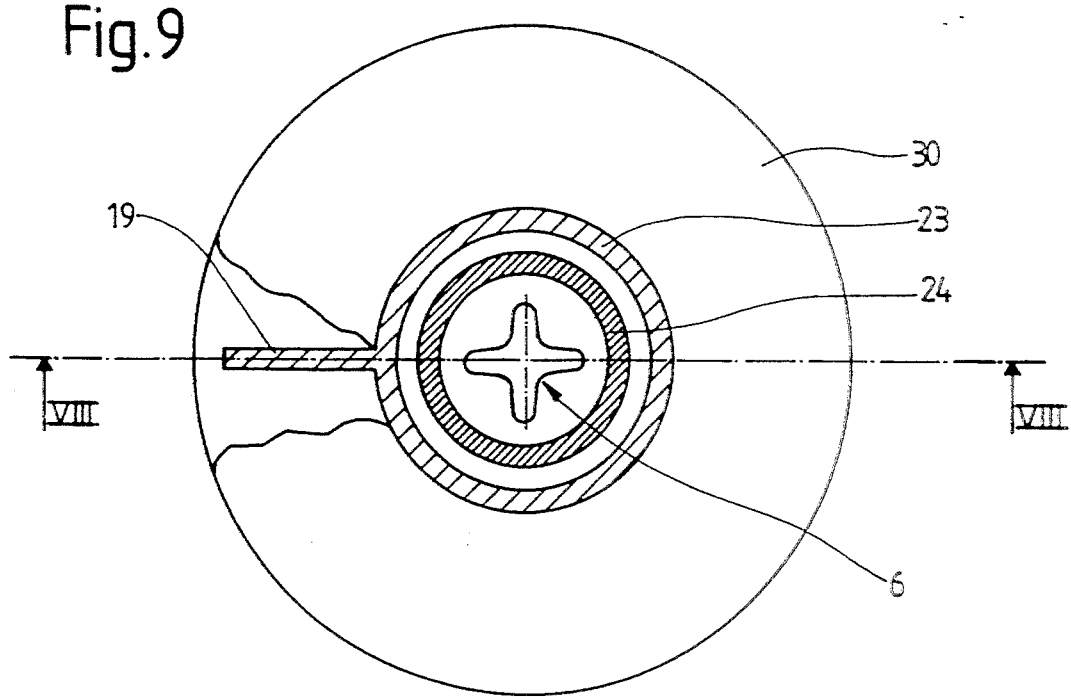
FIG. 9 shows a plan view of FIG. 7 in which part of the insulating covering has been removed.

FIGS. 7, 8 and 9 represent a third embodiment having all the measuring zones 34 on the upper face and the contact zones 23, 24 on the other face, each face having an insulating covering film 29, 30. For this purpose, the radial extension 25 of the current collector 17, shaped like a closed ring located closest to the center, has a small traversing portion 39 linked by a passage 33 to a contact zone 24, located on the other face of the disc, in the form of a closed ring located close to the center of the disc. Similarly, the current collector 16, in the shape of a closed ring situated closest to the periphery on the upper face of the disc, has a small traversing portion 37, joining the radial extension 19 located on the other face, said extensions being terminated by a zone 23 shaped like a closed ring concentric to the ring 24. In this embodiment, the drive device 6 is composed of a central star-shaped opening.

The face of the disc having the current collectors 16, 17 may also have a third collector 18, shown in dotted lines.

Figure 10:
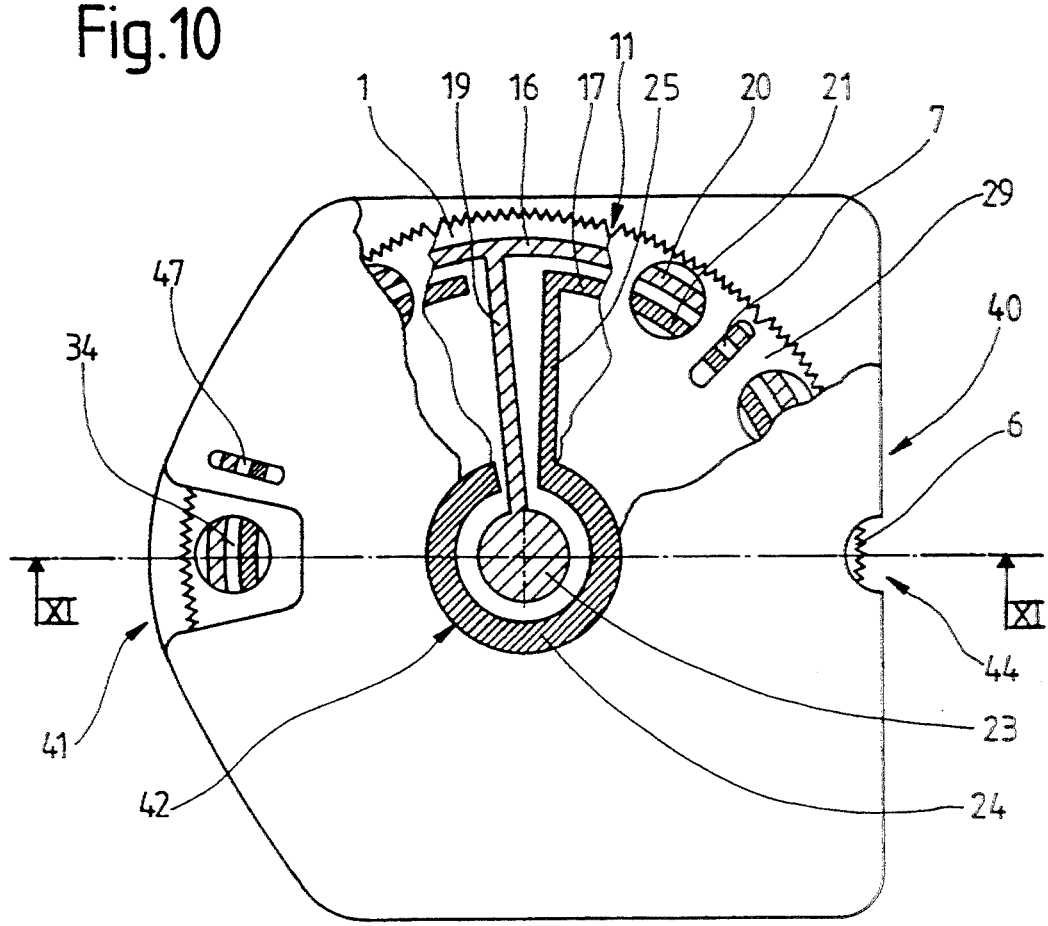
FIG. 10 shows a fourth embodiment in which part of the housing and of the covering of the disc-sensor have been partially removed.
Figure 11:
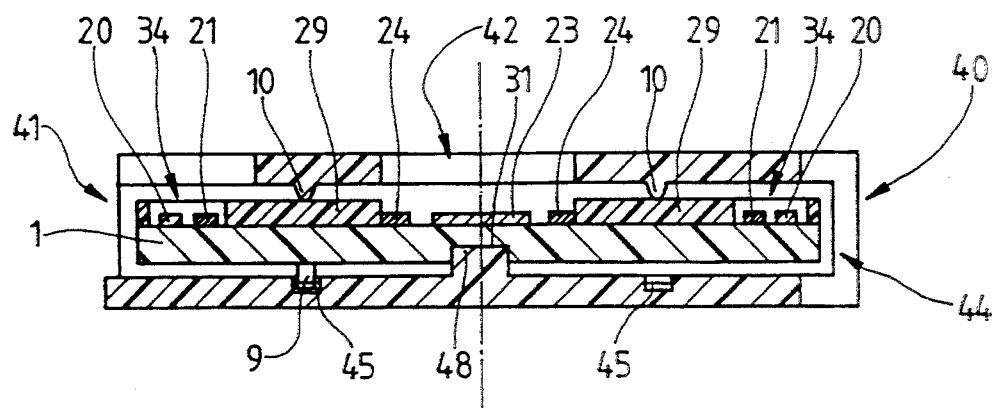
FIG. 11 shows a diametral section of FIG. 10 along the line XI—XI.

FIGS. 10 and 11 show a fourth embodiment of a disc-sensor of the type shown in FIGS. 4 to 6 but having twelve equal circular sectors, said disc-sensor being entirely contained in a housing 40 that makes it possible both to protect the eleven measuring zones 34 and to facilitate its positioning in the measuring apparatus so as to correctly position the first measuring zone to be used, as well as the drive mechanism 6, the contact zones 23, 24, and the windows 7 forming isolating zones for the used measuring zones. In the embodiment shown, the housing is composed of a half-disc and of a half-square bonded along a diameter providing a space inside the housing slightly greater than the diameter of the disc 1. At the extremity of the half-disc in a perpendicular axis to the junction plane of the half-disc and of the half-square, the housing has an opening 41 providing access to a single measuring zone. Close to the opening 41 there is another opening 47, positioned to be located above a window 7 closest to the measuring zone in place in the opening 47. In the center of the disc the housing has an opening 42 providing access to the contact zones 23, 24. In the embodiment shown, the drive mechanism 6 of the disc-sensor is composed of indentations at the edge of the disc-sensor over its entire periphery; the housing 40 then has another opening 44 located on the same axis as the opening 41 and on the half-square of the housing. The opening 41 may also be located at another part of the circumference of the housing as a function of the arrangement of the drive mechanism of the measuring apparatus adapted to cooperate with the indentations of the disc-sensor.

The section of FIG. 11 also shows that the housing 40 makes it possible to maintain the disc-sensor in a predetermined spatial position. For this purpose, the bottom of the housing has at its center a small axle 48 that cooperates with a blind hole 31 of the disc to permit the latter to be centered in the housing 40. In the embodiment shown, the free rotation of the disc in the housing is assured by the cooperation of the bosses 10, no longer supported by the disc, but by the housing, and of the small centering axle 48. The section of FIG. 11 also shows an anti-return device. This anti-return device is composed for example of a small catch 9 carried by the disc 1, adapted to cooperate with a notched groove 45 in the bottom of the housing.

Figure 12:
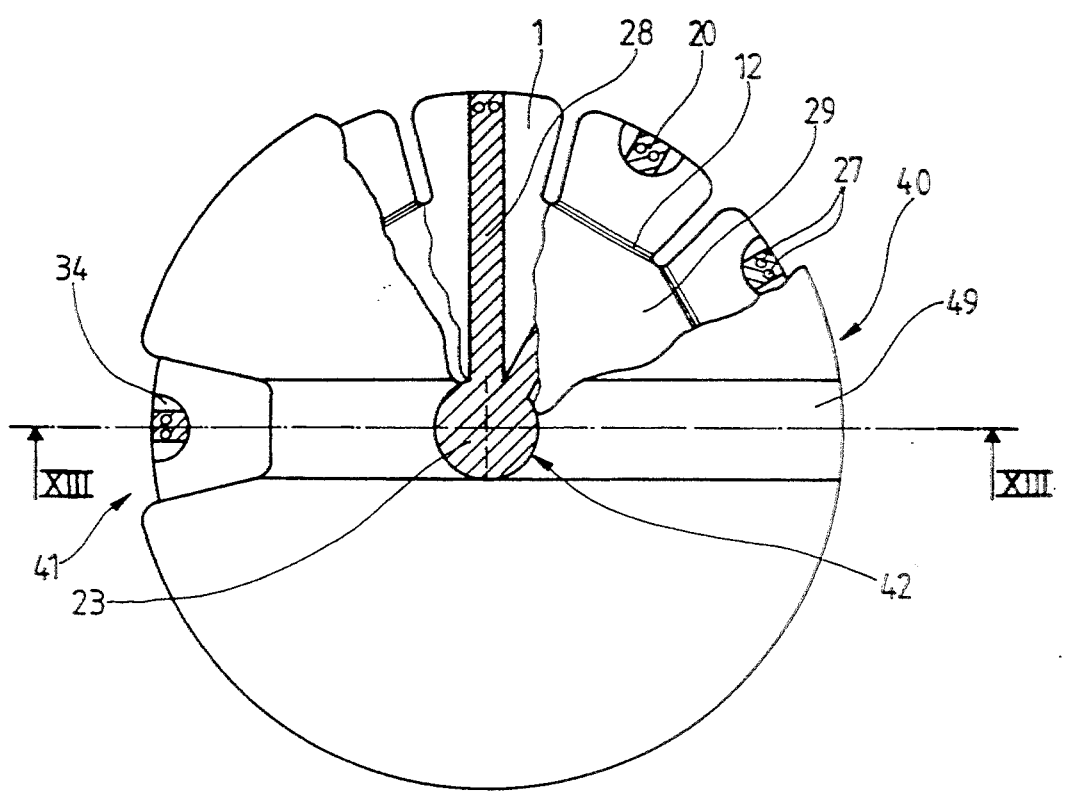
FIG. 12 shows a fifth embodiment in which part of the housing and of the covering of the disc-sensor have been partially removed.
Figure 13:
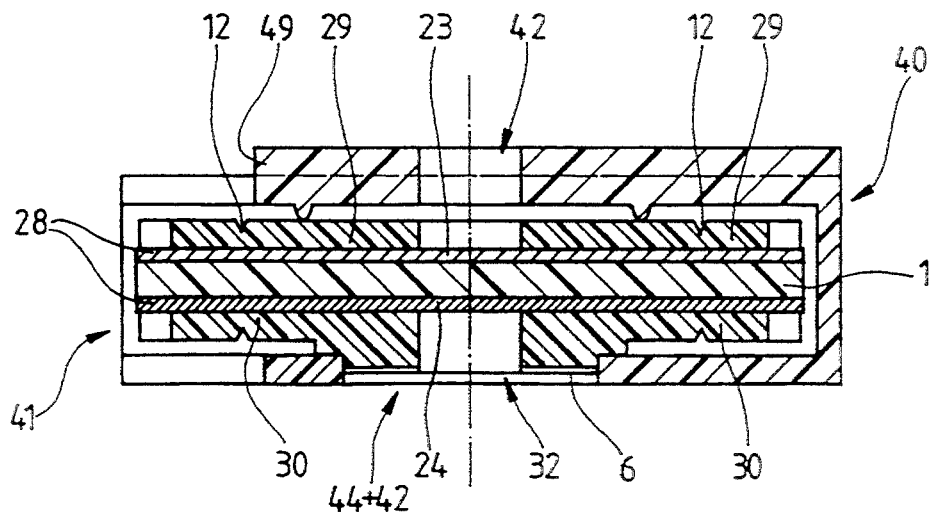
FIG. 13 shows a diametral section of FIG. 12 along the line XIII—XIII.

FIGS. 12 and 13 show a fifth embodiment in which a circular housing contains a disc-sensor of brittle insulating material each face of which supports a current collector 28, the two collectors having the same configuration on each face.

Reference being made to FIG. 12, it appears that each collector 28 is shaped like a star, each branch of which begins as a central disc forming a contact zone 23 or 24 and extends up to the edge of the disc 1 where it constitutes an electrode 20 or 21 (not shown) of a measuring zone 34, the ionic contact between the electrodes being assured by the analytical sample, by moistening around the edge of the disc and/or by capillarity through small traversing orifices 27. In the embodiment shown, each circular sector containing a measuring zone 34 is delimited by the radial notch extending from the edge of the disc up to a weakened zone in the covering 29 or 30, making it possible to break off and totally remove a used measuring zone. The device permitting both the special positioning of the disc inside the housing and its driving is composed of a wheel located on one face of the disc having an annular shoulder for the positioning and a surface provided with radial grooves adapted to cooperate by friction with a corresponding friction crown of the measuring apparatus.

To make it easier to position the sensor in the measuring apparatus, the circular housing 40 also has on its external part opposite that having in its center an opening 44+42 giving access both to the contact zone 24 and to a drive mechanism 6, a rib 49 located in the axis of the opening 41 of the housing and limited by said opening. This rib has at the center of the disc a second opening 42 giving access to the other contact zone 23.

Figure 14:
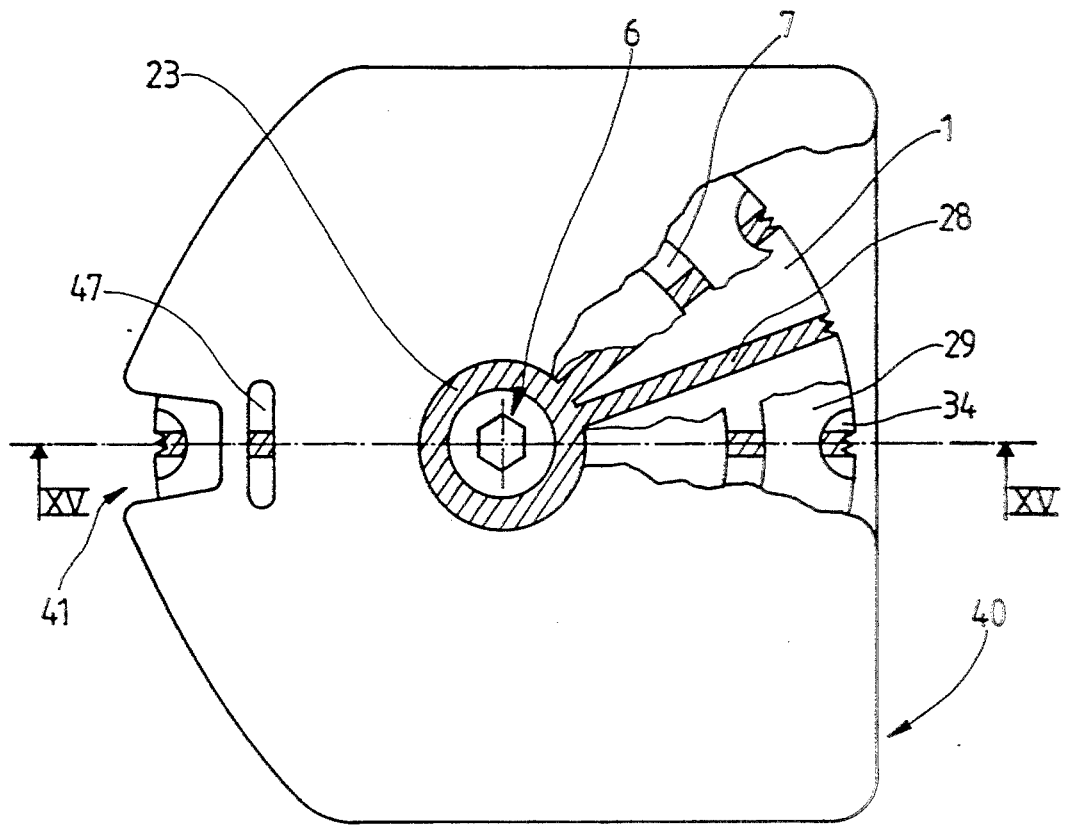
FIG. 14 shows a sixth embodiment in which part of the housing and of the coating of the disc-sensor are partially removed.
Figure 15:
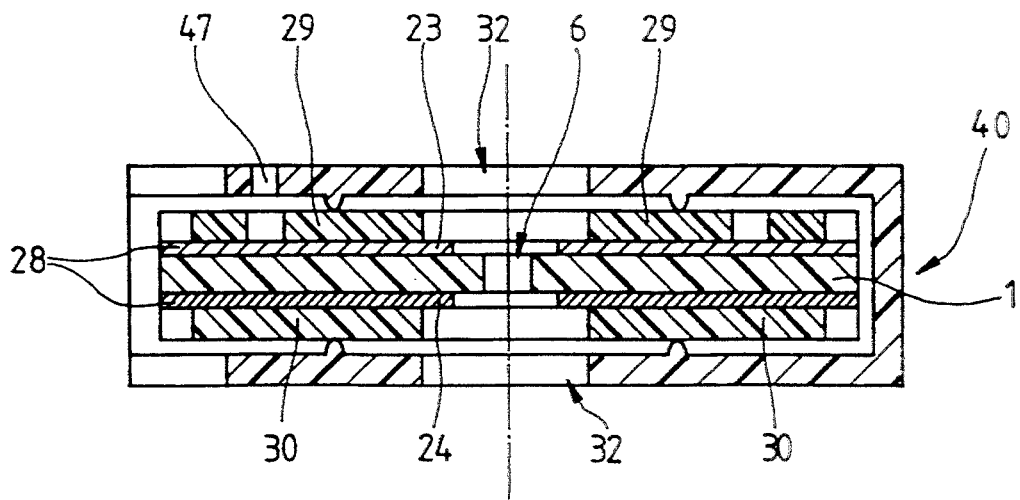
FIG. 15 shows a diametral section of FIG. 14 along the line XV—XV.

FIGS. 14 and 15 show a sixth embodiment of a sensor, the current collectors of which are disposed on each face of the disc according to the previous embodiment, said sensor being contained in a housing of the type described in the fourth embodiment. The contact zones 23, 24 are shaped like two rings, each being disposed on one face of the disc, having at their center a hole of octagonal section traversing the disc and constituting the drive mechanism 6. The windows 7 forming isolating zones are contiguous and constitute a crown where the portions of the branches of the star 28 are open and may be crimped across the opening 47 provided in the housing 40.

Regardless of the embodiment, once placed in a measuring apparatus, the disc-sensor of the invention makes it possible to carry out several measurements with a single sensor before requiring replacement. The measuring apparatus is provided with devices making it possible to connect the current collectors 16, 17 to an electronic measuring and display circuit, to electrically isolate the used zones, to drive the disc in rotation only exposing one single measuring zone at a time.

For the embodiments illustrated in FIGS. 1 to 11, the analysis is carried out by depositing one drop of the sample (for example a drop of blood to measure the glucose level) in a measuring zone 34; once the measurement has been made, the used zone remains on the disc, but is electrically insulated from the other still unused zones by crimping portions of the current collector located between two measuring zones using a stylus integral with the measuring apparatus.

For the embodiment corresponding to FIGS. 12 and 13, a drop of the sample to be analysed is deposited on the edge of the disc, the ionic conduction between the two electrodes being assured by moistening and/or capillarity across the small traversing orifices 27; once the measurement has been effected, the used zone may be totally eliminated by breaking a fragment of the disc along a groove 12. It is also possible, as shown in FIGS. 14 and 15, to crimp one of the branches 28 of the star, as shown for the FIGS. 1 to 11.

As a general rule, the different embodiments described for driving the disc-sensor in rotation, connecting it to a measuring apparatus, localising and positioning the active zones, may give rise to numerous other embodiments without departing from the scope of the instant invention.

What is claimed is:

1. A disposable electrochemical sensor having multiple measuring zones that are sequentially separable, and using a single sensor which is introduced into a measuring apparatus for carrying out several successive measurements of the same physico-chemical characteristic or of a concentration of the same component present in a solution, an effluent or a fluid, said sensor comprising:

a thin, insulating rigid support in the shape of a disc;

at least two current collectors of identical or different conducting materials arranged on the disc to be insulated from each other and each having portions or extensions situated in a peripheral border adjacent to the periphery of the disc, said portions or extensions forming electrodes in the measuring zones connected to each other by a corresponding one of said current collectors, and each of said current collectors extending up to a zone close to the center of the disc where said current collector has a terminal part shaped to provide a contact zone;

drive means for rotating the disc; and guide means for positioning the measuring zones in the measuring apparatus and for isolating a used measuring zone from the other, still unused, measuring zones.

2. A sensor according to claim 1, wherein the two current collectors are supported by the same face of the disc and are shaped as two concentric rings disposed inside the peripheral border, the ring located closest to the center of the disc is open, and each ring has a radial extension directed towards the center of the disc to provide a contact zone.

3. A sensor according to claim 2, which has a third current collector having a concentric portion close to the two first collectors and a radial extension directed towards the center of the disc to provide a third contact zone.

4. A sensor according to claim 1, wherein the two current collectors are supported by the same face of the disc and are shaped as two closed concentric rings arranged inside the peripheral border, the ring located closest to the center of the disc having a radial extension supported by the same face of the disc and directed towards the center thereof and the ring closest to the edge of the disc having a radial extension supported by the other face of the disc and joined to said edge ring by a current collector portion traversing the disc.

5. A sensor according to claim 4, which has a third current collector having a concentric portion close to the two first collectors and a radial extension directed towards the center of the disc to provide a third contact zone.

6. A sensor according to claim 1, wherein the two current collectors are supported respectively by each face of the disc and are each shaped like a star, each branch of said star emanating from a disc or from a central crown forming a contact zone and extending up to the edge of the disc.

7. A sensor according to claim 6, wherein the measuring zones have traversing orifices assisting by capillarity the ionic junction of the electrodes carried by each face of the disc.

8. A sensor according to claim 1, wherein the contact zones are in the shape of a pastille, a disc or an open or a closed ring situated on the same face of the disc or respectively on each face of it.

9. A sensor according to claim 1, wherein the measuring zones are regularly distributed on the disc in all or part of substantially equal circular sectors, and wherein the perimeter of said measuring zones is delimited, either by a deformation of the insulating support disc, or by windows in an insulating film covering the disc.

10. A sensor according to claim 1, wherein the current collectors are composed of bands obtained by thin or thick layer deposition of a conducting material or by lamination of a covered insulating film of a conducting material, and said conducting material is gold, silver, platinum, nickel, palladium, titanium or carbon.

11. A sensor according to claim 10, wherein one current collector is of platinum and constitutes a working electrode, and wherein the other current collector is of silver/silver chloride and constitutes a reference electrode.

12. A sensor according to claim 11, wherein the working electrode is coated with a reagent having at least one enzyme specific to the component present in the solution.

13. A sensor according to claim 12, wherein the reagent has a mediator.

14. A sensor according to claim 1, wherein the rigid insulating material constituting the disc is a vinyl resin, a ceramic, mica, a polyethylene terephthalate or a glass.

15. A sensor according to claim 1, wherein the drive means comprises a central polygonal traversing hole, a toothed crown for driving the disc by means of gears or friction and located on one of its faces, or indentations at the edge of the disc.

16. A sensor according to claim 1, wherein the guide means for the measuring zones comprises recesses regularly spaced in the thickness of the circumference of the disc.

17. A sensor according to claim 1, wherein the disc has on one of its faces a portion of a radial rib arranged to cooperate with an abutment located in the measuring apparatus to prevent the disc from rotating more than 360°.

18. A sensor according to claim 1, wherein the disc has an anti-return catch.

19. A sensor according to claim 1, wherein the disc has a thickness between 0.5 and 6 mm and a diameter between 5 and 15 cm, and wherein the sensor comprises between 6 and 24 of said measuring zones.

20. A sensor according to claim 1, which has a housing provided with openings giving access to at least one of said measuring zones and to an associated isolating zone, to the contact zones and to the drive means, and said housing is a protection means and a positioning means of the sensor in the measuring apparatus.

* * * * *